United States Patent [19]
Malmqvist et al.

[11] Patent Number: 5,972,612
[45] Date of Patent: Oct. 26, 1999

[54] SURFACE-SENSITIVE DETECTION OF HYBRIDIZATION AT EQUILIBRIUM

[75] Inventors: Magnus Malmqvist; Björn Persson, both of Uppsala, Sweden

[73] Assignee: Biacore AB, Uppsala, Sweden

[21] Appl. No.: 08/983,108

[22] PCT Filed: Jul. 12, 1996

[86] PCT No.: PCT/SE96/00949

§ 371 Date: May 15, 1998

§ 102(e) Date: May 15, 1998

[87] PCT Pub. No.: WO97/04129

PCT Pub. Date: Feb. 6, 1997

[30] Foreign Application Priority Data

Jul. 14, 1995 [SE] Sweden .................................. 9502608

[51] Int. Cl.⁶ .............................. C12Q 1/68; G01N 33/48
[52] U.S. Cl. .................................................. 435/6; 436/94
[58] Field of Search ..................... 435/6; 436/94

[56] References Cited

U.S. PATENT DOCUMENTS 5,552,270  9/1996  Khrapko et al. ............................. 435/6

OTHER PUBLICATIONS

Nilsson et al., Analyt. Biochem. 224, 400–408 (Jan. 1995).
Stimpson et al., Proc. Natl. Acad. Sci. USA 92, 6379–6383 (Jul. 1995).
Persson et al., Analyt. Biochem. 246, 34–44 (1997).
Stimpson et al., Genetic Analysis Biomolec. Eng. 13, 73–80 (1996).
Gotoh et al., DNA Res. 2(6), 285–293 (Dec. 1995)(abstract only).

*Primary Examiner*—Kenneth R. Horlick
*Attorney, Agent, or Firm*—Seed and Berry LLP

[57] ABSTRACT

A method of analysing nucleic acid sequences comprises measuring by surface sensitive detection technique the binding interaction between a first nucleic acid sequence and a second nucleic acid sequence, one of the first and second nucleic acid sequences being immobilized to a solid phase surface, to determine the affinity or an affinity related parameter for the binding reaction as indicative of the extent of complementary between the first and second nucleic acid sequences. The method is characterized in that the measurement of the binding interaction is performed at annealing conditions adjusted such that the dissociation rate constant for the binding interaction corresponding to full complementarity between the first and second nucleic acid sequences is greater than about $10^-$ per second, thereby permitting equilibrium for the interaction to be rapidly attained.

14 Claims, 8 Drawing Sheets

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:1:

TTTTTTTTGC ATCTTATTTT TTTT                                              24

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:2:

TTTCCTCAGC ATCTTATCCG AGTTT                                             25

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:3:

TTTCCTCAGC ATTTTATCCG AGTTT                                             25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

TTTCCTCAGC AACTTATCCG AGTTT                                             25

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:5:

TTTGGAGTCG TACTTATCCG AGTTT                                             25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

TTTCGAGTCG TACTTATCCG AGTTT                                                     25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:7:

TTTCCAGTCG TAGTTATCCG AGTTT                                                     25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:8:

TTTCCTGTCG TAGATATCCG AGTTT                                                     25

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:9:

TTTCCTCTCG TAGAAATCCG AGTTT                                                     25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

TTTCCTCACG TAGAATTCCG AGTTT                                                     25

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

TTTCCTCAGG TAGAATACCG AGTTT                                                     25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

```
TTTCCTCAGC TAGAATAGCG AGTTT                                            25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:13:

TTTCCTCAGC AAGAATAGGG AGTTT                                            25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:14:

TTTCTTCAGC AAGAATAGGC AGTTT                                            25

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:15:

TTTCTTCAGC AACAATAGGC TGTTT                                            25

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

TTTCCTCTCG TAGATATCCG AGTTT                                            25

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:17:

TTTCCTCACG TAGAAATCCG AGTTT                                            25

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:18:

TTTCCTCAGC AAGAATAGGG AGTTT                                            25
```

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:19:

TTTCCTCAGC AACAATAGGC AGTTT                    25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:20:

TTTCCTCACG TTGAATTCCG AGTTT                    25

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:21:

TTTCCTCACG TAAAATTCCG AGTTT                    25

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:22:

CCTCAGCATC TTATCCGAG                          19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:23:

CCTCATCATT TTATCCGAG                          19

(2) INFORMATION FOR SEQ ID NO:24:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:24:

GTAGAATATT T                                    11

-continued (2) INFORMATION FOR SEQ ID NO:25:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:25:

AGTCGTAGTT T                                                                       11

(2) INFORMATION FOR SEQ ID NO:26:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:26:

GAATAGGCTT T                                                                       11

SURFACE-SENSITIVE DETECTION OF HYBRIDIZATION AT EQUILIBRIUM

FIELD OF THE INVENTION

The present invention relates to an improved method of nucleic acid sequencing based on the detection and measurement of hybridization interactions.

BACKGROUND OF THE INVENTION

The generation of DNA sequence information has dramatically increased due to the large programs for sequencing of the human genome. Today that work is mainly done by traditional gel electrophoretic separation of DNA fragments terminated at different positions, either enzymatically (dideoxy chain termination method according to Sanger et al., Proc. Natl. Acad. Sci. USA 74: 5463–5467 (1977)) or chemically (chemical degradation method according to Maxam and Gilbert, Proc. Natl. Acad. Sci. USA 74: 560–564). These systems are, however, both time- and labour-intensive.

There is therefore a general need for more effective methods for de novo sequencing of DNA as well as for repeated sequencing of known sequences for analysis of mutations, such as point mutations. The mutation analysis will increase as more information will be gathered about the correlation between different diseases and mutations and also due to the need to verify deliberately introduced mutations in biotechnology work.

Sequencing by hybridization (SBH) (see e.g. Drmanac et al., Genomics 4: 114; Strazoski et al., Proc. Natl. Acad. Sci. USA 88: 10089 (1991); Bains and Smith, J. Theoretical Biol. 135: 303 (1988); and U.S. Pat. No. 5,202,231) has become an interesting alternative to traditional sequencing with a potential for higher through-put of information. This type of system utilizes the information obtained from multiple hybridizations of the polynucleotide of interest, using short oligonucleotides to determine the nucleic acid sequence. However, there are several technical problems associated with this technology. For example, while today there are ways to build arrays of oligonucleotides on a chip based on the synthesis of oligoprobes and photolitographic techniques, it is still complicated to provide on a chip the large set of oligonucleotide probes required for determining a random nucleic acid sequence. Further, the detection of interaction of labelled target DNA is normally done by fluorescent or radioactivity measurements. Such detection is dependent on washing of the chip to get rid of residual labelled target molecules and the oligoprobes must therefore bind rather strongly to the target molecules. There are also problems with the binding of oligoprobes with a single base mismatch in combination with the different sensitivity to washing conditions dependent on base pair composition, G:C being more stable than A:T. One attempt to overcome such problems is to use tetraalkylammonium salts that eliminate the difference in stability of G:C and A:T base pairs.

Even if differences in base composition can be compensated for, the whole SBH procedure is based on interaction, washing, and detection of hybridized target DNA and oligoprobe. The conditions for the hybridization thus have to be adjusted for a stable hybridization which can be detected only after several washing cycles. Dependent on the position of the mismatch of single bases, base composition, oligoprobe length and temperature, there will be several hybridizations of oligomers that will show up as weaker binding and such interactions will be problematic to determine. Temperature and salt gradients elution have been suggested but are difficult to elaborate technically.

Due to the conditions needed for hybridization there is also always a potential risk for the target DNA to hybridize to itself due to complementary regions of the DNA.

A major disadvantage of SBH is, however, that the information is exclusively based on short-range information and the fact that overlaps are unique. Success is dependent on whether or not there are repeated sequences in the nucleic acid to be analysed. The need and importance of repeated sequences are known from several situations, not least in the analysis of genes like, for example, the gene for Huntington's disease where repeated sequences and the amount of repeats have clinical relevance.

For the analysis of known sequences or of a particular site, mutation analysis may be advantageous. An example of this is the mutation dependent tumour frequency found for proteins such as p53. Binding of p53 to DNA is crucial for a correct control of cell growth and mutation dependent methods for therapy are likely to be developed. Furthermore, the kind of mutation detected may affect the treatment and aid in selecting the appropriate drug.

Label-free real-time measuring techniques, such as those based on surface plasmon resonance (SPR), have been used to study the hybridization of DNA and oligomeric probes (oligoprobes). Attempts have also been made to analyse the kinetic information of the hybridization to determine the degree of hybridization, e.g. to detect mutant sequences, as described in Biosensor Application Note 306, 1994, Pharmacia Biosensor AB, Sweden. It has, however, been found that such analyses are difficult to use for obtaining relevant mismatch information as the kinetics for hybridization is complex under the conditions for hybridization normally used, which result in the formation of relatively stable hybridization complexes with long half-lives.

WO 93/25909 discloses the use of label-free techniques mentioned above in combination with immobilised receptors, specifically antibodies, which are selected or designed to have a high dissociation constant, or "off-rate", for the binding of analyte to the receptor. Such a detection system will rapidly respond to changes in the analyte concentration and regeneration of the sensing surface supporting the receptor will not be required. Typically, the receptor is selected such that the dissociation rate constant ($k_{off}$ or $k_{diss}$) for a particular analyte of interest is higher than $10^{-2}$ per second.

WO 95/00665 discloses a method of providing the sequence of a single stranded nucleic acid molecule, which when hybridized to a complementary single stranded molecule results in a double (duplex) structure having a preselected value for a free energy parameter, such as ligand binding, melting temperature or affinity for a target sequence. Thereby nucleic acid molecules may be produced which are tailored for specific applications, e.g. nucleic acid molecules with a defined affinity for a ligand which binds to the DNA and regulates the expression of a protein encoded by the nucleic acid.

SUMMARY OF THE INVENTION

One object of the present invention is to provide a nucleic acid sequencing method based on hybridization interactions at a solid phase surface, which method is more rapid to perform than the prior art methods and which may not require regeneration of the surface between measurements.

Another object of the invention is to provide a sequencing method which is more sensitive than the prior art methods to obtain mismatch information, i.e. in determining whether there is full complementarity between hybridizing nucleic acid fragments or not.

Still another object of the invention is to provide a sequencing method which permits the use of short oligonucleotide probes.

Another object of the invention is to provide a sequencing method which permits the detection of repeated sequences.

Yet another object of the invention is to provide a sequencing method which is less susceptible to the presence of complementary regions in a target nucleic acid sequence.

It has now according to the present invention been found that the above and other objects and advantages may be attained by providing for reaction conditions which, on one hand, give lower affinity but, on the other hand, permit rapid association and dissociation in the hybridization interactions at the surface. More particularly, the reaction conditions should be selected such as to obtain a high dissociation rate constant for the hybridization event.

In contrast to the above-mentioned WO 93/25909 which describes a high dissociation rate obtained by selection or design of molecular properties of the receptor, the present invention provides for the desired high dissociation rate by appropriate adjustment of the reaction conditions.

The present invention thus relates to a method of analysing nucleic acid sequences, which method comprises measuring by surface sensitive detection technique the binding interaction between a first nucleic acid sequence and a second nucleic acid sequence, one of the first and second nucleic acid sequences being immobilized to a solid phase surface, to determine the affinity or an affinity related parameter for the binding reaction as indicative of the extent of complementarity between the first and second nucleic acid sequences. The invention is characterized in that the measurement of the binding interaction is performed at annealing conditions adjusted such that the dissociation rate constant for the binding interaction corresponding to full complementarity between the first and second nucleic acid sequences is greater than about $10^{-3}$ per second, thereby permitting equilibrium for the interaction to be rapidly attained.

The term nucleic acid is to be interpreted broadly and in addition to DNA and RNA also includes nucleic acid analogues, such as modified DNA or RNA, or other hybridizing nucleic acid like molecules, such as PNA (peptide nucleic acid).

The term annealing as used herein refers to the combination and interactions of two complementary nucleic acids.

The first and second nucleic acids may each be single-or double-stranded, or single-stranded DNA or RNA complexed with a different molecule, such as a modified nucleic acid, PNA, a peptide, etc.

In a preferred embodiment, the dissociation rate constant is higher than about $10^{-2}$ per second, especially higher than about $10^{-1}$ per second.

Other preferred embodiments of the invention are described below.

DETAILED DESCRIPTION OF THE INVENTION

The present invention thus relates to the analysis of the interaction between a first nucleic acid and a complementary second nucleic acid under annealing conditions where high kinetic (dissociation rate) constants are present in the interaction and equilibrium of the reaction therefore can be achieved rapidly, i.e. that the reaction will readily reach equilibrium within a reasonable time during the experiment. This is valid for the formation of e.g. DNA—DNA dimers as well as sequence dependent formation of other complexes of nucleic acids.

The necessary conditions for the desired high dissociation rate may be obtained by proper selection of one or more of (i) the solvent, ionic strength and/or pH, (ii) the reaction temperature and (iii) the nucleic acid probe length. In the second case (ii), which is presently preferred, a reaction temperature is selected which is closer to the melting temperature, Tm, in the annealing of complementary DNA fragments than used in conventional hybridization assays for the particular chemical environment or above the melting temperature ("Tm" being the temperature at which half of the hybridization is lost at equilibrium). The annealing of the nucleic acids reflects the response obtained for a particular affinity at the conditions used and the relative affinity can be determined with high precision.

Thus, for a certain interaction, the dissociation rate constant ($k_{diss}$) is dependent on the reaction temperature or the reaction medium. While the equilibrium response level may be controlled by selection of nucleic acid concentration, the reaction kinetics will be dependent on the temperature and the reaction medium.

The method of the invention may be performed by analysing the interaction of either (i) the target nucleic acid, such as a target DNA, over different oligomeric probes, such as oligoDNA probes, immobilized on the solid phase surface, or in other words, sensing surface, or (ii) a series of oligomeric probes over a surface having a target nucleic acid immobilized thereon.

It is readily understood that under standardized conditions with known solution concentrations, a single determination for each oligoprobe and target molecule, respectively, may be sufficient for a comparison to a standard value. As is per se known in the art, by using a concentration close to the inverse of the affinity constant, the sensitivity to changes in affinity will be at its maximum.

There are several advantages of working at annealing conditions closer to the melting temperature than that conventionally used for hybridization or above that, as will be explained below.

With reference first to method aspect (i) above with oligoprobes immobilized on the sensing surface, this variant may be performed sequentially with a different single oligoprobe immobilized on the sensing surface or with an array of different oligoprobes immobilized.

With dissociation rate constants higher than about $10^{-3}$ s$^{-1}$ the equilibrium will be reached rapidly, and there may be no need for regeneration of the oligoprobe—supporting sensing surface as the complex formed at the surface will dissociate within a few minutes spontaneously. The affinity can thus rapidly be determined and a new sample of target nucleic acid can be analysed without regeneration of the sensing surface.

By using a series of oligoprobes, each representing a part of a known sequence, mutations in the target DNA can be analysed as a decrease in affinity for the particular oligoprobe interaction with the target nucleic acid, and the position for the mutation may also be identified, as will be described in more detail below. If all possible combinations of oligoprobes can be analysed, it is readily understood that not only the position for a mutation can be determined but also the base change in question.

Measurements of affinity of the interaction under such annealing conditions that provide for a high dissociation rate constant will also reduce problems associated with target nucleic acid intramolecular complementary structures, as the latter will have a lower tendency to be formed under rapid kinetic conditions and be under exchange with the immobilized oligomeric nucleic acid on the surface.

Another problem usually experienced in sequencing by hybridization (SBH) is to obtain a good nucleic acid preparation and to know the concentration of the amount of active nucleic acid, the term "active" referring to the hybridization capability. Under conditions of continuous flow and a diffusion rate limited association, the initial association of target DNA to an immobilized oligoprobe will be concentration dependent and can be used for concentration determination of the active target DNA. Such a concentration determination will be required for correlating the affinity measurements to literature data.

The well-known prior art problem in sequencing by hybridization related to the presence of repeated sequences can also be overcome by the present procedure of affinity measurements under annealing conditions with high dissociation rate constants. Since a repeated sequence can interact with different oligoprobes immobilized on the sensing surface, the avidity effects of such multiple interactions will give rise to a higher "apparent" affinity than expected and a much smaller "apparent" dissociation rate constant. The affinity determinations will thus be sensitive for repeated sequences as an increase in apparent affinity, whereas a decrease in affinity will be correlated to a mismatch.

The above described first method aspect of the invention, where an oligoprobe is immobilized on the sensing surface and a larger nucleic acid fragment to be sequence analysed is present in solution, is suitable for large arrays of oligoprobes and a detection system that can analyse a large amount of interaction at the same time. However, the reversed analytical situation according to the abovementioned second method aspect relating to the sequential analysis of oligoprobe interactions with immobilized target nucleic acid is also useful.

Under such conditions, for example, the amount of repeated sequences can be correlated to the amount of bound oligoprobes as long as they react independently of each other. In this way repeated sequences can be quantified and will not be dependent on avidity effects as mentioned above.

The increase in binding due to several binding positions on the immobilized target nucleic acid can therefore be described with the same dissociation rate constant as the single interaction, in contrast to the case of a multiple interaction with target nucleic acid in solution where the interactions with several different oligoprobes immobilized on the surface will give rise to an increased signal coupled to a lower dissociation rate constant.

Since in the present invention, association rate is used to measure the concentration of the analyte, the equilibrium response level will be a measure of affinity, a complete match of hybridizing sequences having a higher afffinity than a mismatch. A higher equilibrium level with the same dissociation rate constant will therefore be a measure of the amount of repeated sequences, whereas an increase in signal in combination with a smaller "apparent" dissociation rate constant will be a measure of multiple interaction for that sequence. Information from the dissociation part of the interaction can thus be used in combination with the affinity measurement for verification of the interaction and to make the method as sensitive as possible for detecting a mismatch.

To identify positions for a mutation in a nucleic acid fragment, such as a DNA fragment, it may be advantageous to use a scanning approach. If the mutation position is unknown, an exemplary procedure may be as follows:

The DNA fragment is immobilized on the sensing surface.

The position for the mutation is then scanned by sequentially contacting the surface with solutions of oligoprobes, each covering a respective part of the whole DNA target molecule.

The part or parts of the DNA target which are found to contain a mutation are then subjected to a detailed analysis of the position of the mutation by overlapping probe analysis in a "minisequencing" format.

The identity of the base mutation may then be determined by testing the four base variants (A, C, T and G) of an oligoprobe with respect to the mutated position. If desired, this last step can be done directly in the above minisequencing format if all possible combinations of oligoprobes are tested.

The above described procedure may be beneficial as sequencing analyses often will be done with samples which do not contain any mutations therein and it is understood that the described scanning approach can be a very rapid procedure.

A corresponding scanning procedure may, of course, be performed in the reversed mode with the oligoprobes immobilized on the surface and the target nucleic acid in solution.

The surface sensitive detection used in the method of the invention may be obtained by various detection systems. In a suitable type of detection system, a change in a property of the sensing structure is measured as being indicative of binding interaction at the sensing surface. Among these methods are, for example, mass detecting methods, such as piezoelectric, optical, thermo-optical and surface acoustic wave (SAW) methods, and electrochemical methods, such as potentiometric, conductometric, amperometric and capacitance methods. It is also possible to use short range radioactivity, such as scintillation plastics in close proximity to the interaction position of $^3H$ or other short range ionising radiation.

Among optical methods may particularly be mentioned those that detect surface refractive index, such as reflection-optical methods, including both internal and external reflection methods, e.g. ellipsometry and evanescent wave spectroscopy (EWS), the latter including surface plasmon resonance spectroscopy (SPRS), Brewster angle refractometry, critical angle refractometry, frustrated total reflection (FTR), evanescent wave ellipsometry, scattered total internal reflection (STIR), optical wave guide sensors, evanescent wave based imaging, such as critical angle resolved imaging, Brewster angle resolved imaging, SPR angle resolved imaging, etc., as well as methods based on evanescent fluorescence (TIRF) and phosphorescence.

Among the optical methods mentioned above, especially SPRS has attracted much attention recently. The phenomenon of SPR is well known. In brief, SPR is observed as a dip in intensity of light reflected at a specific angle from the interface between an optically transparent material, e.g. glass, and a thin metal film, usually silver or gold, and depends on among other factors the refractive index of the medium (e.g. a sample solution) close to the metal surface. A change of refractive index at the metal surface, such as by the adsorption or binding of material thereto, will cause a corresponding shift in the angle at which SPR occurs. To couple the light to the interface such that SPR arises, two alternative arrangements may be used, either a metallized diffraction grating (Wood's effect), or a metallized glass prism or a prism in optical contact with a metallized glass substrate (Kretschmann effect). For further details on SPR, reference is made to our WO 90/05295.

The measurements in the present invention are preferably performed in a flow system type biosensor, permitting rapid kinetics to be identified. An example of such a biosensor system is the BIAcore® system (marketed by Pharmacia Biosensor AB, Uppsala, Sweden).

The present invention will now be illustrated by the following non-limiting Examples, reference also being made to the accompanying drawings.

EXAMPLES

The experimental work described below is essentially based on the hybridisation of oligonucleotide probes having matching 8-mer sequences. The target oligonucleotide was in no case exceeding the size of a 50-mer. A set of reagents with oligosequences derived from exon 6 of the p53 gene was used. Hybridisations were performed in two formats, either straight, i.e. the probe (the 8-mer) in solution and the target DNA on the surface, or reversed, with the probe on the surface and the target in solution.

MATERIALS AND METHODS

The analytical instrument used for the analyses was either a BIAcore® or a BIAcore ® 2000 system (Pharmacia Biosensor AB, Uppsala, Sweden), which are biosensor systems based on SPR and having four flow channels. As sensing surface was used Sensor Chip CM5 or SA5, both with instrument immobilised streptavidin (SA), or Dx500 or Dx40 matrices with batch immobilised SA.

Generally, a buffer consisting of 10 mM Hepes, 0.5 M NaCl, 3.4 mM EDTA, 0.002% Surfactant P20, pH 7.4 was used for hybridisation. The same buffer was used for capturing of biotinylated ligands. The ligand concentration used for capturing was ~1 $\mu$g/ml. Variable contact times were used to control ligand surface concentrations. Oligonucleotides, denoted "BP" or "NIPE", were purchased from Pharmacia Biotech AB, Uppsala, Sweden (BP1–69), Scandinavian Gene Synthesis, Köping, Sweden (NIPE8, 19–22) or KEBO Lab, Stockholm, Sweden (NIPE32–36).

When necessary, HCl, pH 2.15, was used for the regeneration of the surface between each hybridisation cycle. The hybridisation temperature was 25° C. The equilibrium response ("$R_{eq}$") was obtained by taking the report point at steady-state in an active flow cell, subtracted by the corresponding value in a flow cell without captured oligonucleotide. The $R_{eq}$-response for each probe concentration was exported to the BIAeval™ software (Pharmacia Biosensor AB) and the affinity was determined by a non-linear procedure. A contact time of three minutes and a flow rate of 15 $\mu$l/min was used for a typical cycle of analysis. The hybridisation studies were performed either (i) with a biotinylated target on the surface and 8-mer probes in solution or (ii) with biotinylated probe on the surface and the target molecule in solution. These procedures are referred to as "straight" and "reversed" mode, respectively.

Example 1

Hybridization of Different Oligoprobes to Immobilized Target DNA Under Equilibrium Conditions The following oligonucleotides were tested:
NIPE32: 3' CGTAGAAT (fully matched)
NIPE33: 3' G-------
NIPE34: 3' _-------
NIPE35: 3' -------G
NIPE36: 3' -------_
"-" indicates the same base as the fully matched sequence, and "_" indicates no base.

The following target DNA sequence was used: BP22: 5' Bio TTTTTTTTGCATCTTATTTTTTTT SEQ ID NO: 1, where "Bio" indicates a biotin label.

Hereinafter, "RU" refers to resonance units, and "Fc1" refers to flow channel 1, etc.

Figure 1:
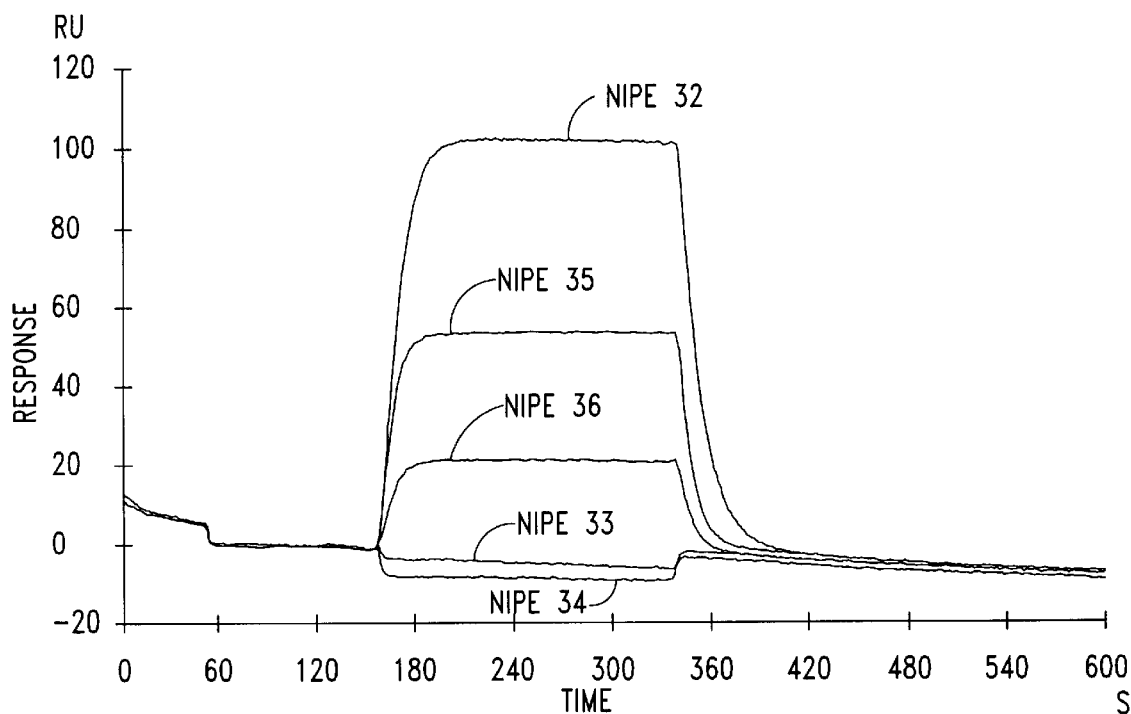
FIG. 1 is an overlay plot of sensorgrams (response vs time) for the hybridization of matching as well as mismatching 7- and 8-mers (NIPE32–36) to an immobilized target DNA sequence (BP22).

BP22 was captured (1523 RU) in Fc1 on a SA5 chip and 0.4 $\mu$M probe was hybridised. The results are shown in FIG. 1. As appears from the Figure, the 3'-end mismatch does not bind, while the 5'- dito binds, but not as strongly as the matched 8-mer. Of the 7-mers, NIPE36 binds, but not NIPE34, which might reflect the different GC-contents, 3/7 and 2/7, respectively. $R_{eq}$ -responses were taken as the flow cell difference Fc1–Fc2.

Figure 2:
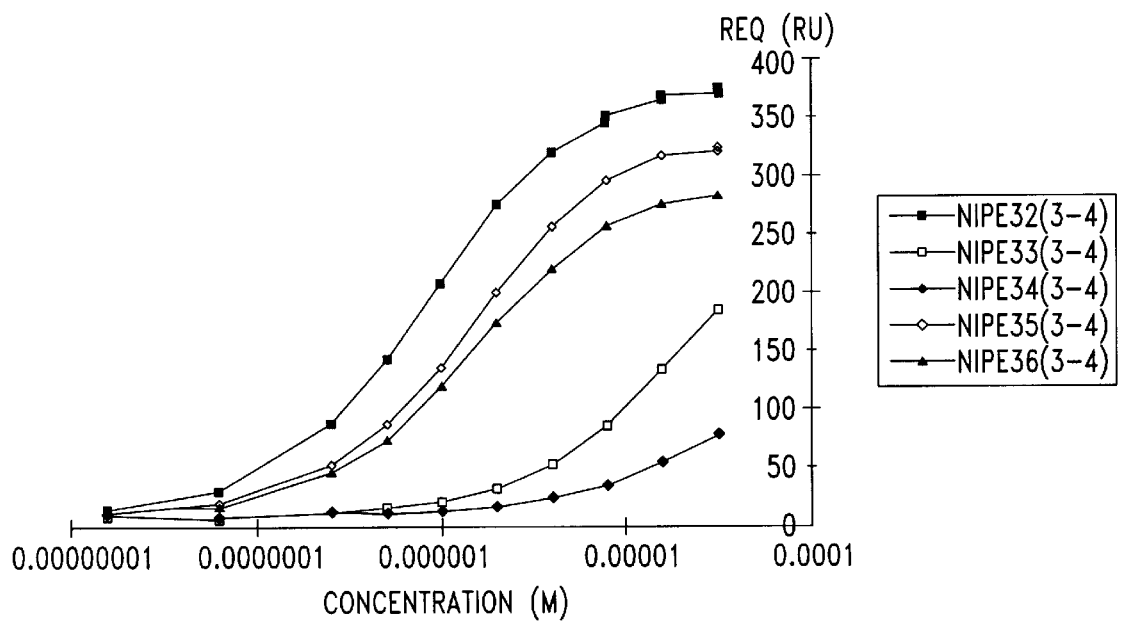
FIG. 2 is a plot of binding curves (equilibrium responses vs concentration) for different concentrations of the oligoprobes in the hybridization in FIG. 1.

BP22 was then captured on SA5 at different surface concentrations: Fc1, 2, 3 & 4 with 296, 808, 1314 and 0 RU, respectively. Then, NIPE 32–36 were passed serially over the chip at concentrations of 15 nM–32 μM. In FIG. 2, all probes (NIPE32–36) are compared with $R_{eq}$-responses plotted vs. concentration. As can be seen in the Figure, NIPE32, 35 and 36 reach $R_{max}$ at a high concentration and it is possible to determine the affinities. The equilibrium dissociation constant ($K_D$) was 0.85, 1.5 and 1.5 μM, respectively. The 3'-end mismatch (NIPE33) and the 7-mer (NIPE34) had much lower affinities. As seen from the Figure, the $R_{max}$ value for NIPE35 is ~15% lower than for NIPE32. This is probably an effect of loss of ligand or sub-optimal regeneration with each cycle. The baseline drift was on average 0.7 RU/cycle over 100 cycles and the probes were run in order starting with NIPE32 and ending with NIPE36. With 1300 RU of a 24-mer ligand, 430 RU of an 8-mer probe would be expected to bind. At $R_{max}$, 380 RU were bound, e.g. a near 90% occupancy. When NIPE35 comes in, after 60 cycles, ligand concentration may be decreased, but also, some previously hybridised probe may have got stuck on the target, thus decreasing the active surface concentration. The lower response of NIPE36 is probably an effect of the lower molecular weight.

A second set of probes was then constructed with 8-mer oligonucleotides, covering the whole target molecule with one base shift per probe. Three biotinylated target molecules based on the p53 system were also constructed, one "wild-type" to which all probes were fully matched and two targets with either a substitution of C for T or T for A.

BP57 and 58 have A or T in either end and should be compared with BP51. Correspondingly, BP59 and BP60 have a G or C in either end and should be compared with BP55. BP61 and 62 are fully matched to the "mutants" BP46 and BP45, respectively.

Figure 3:
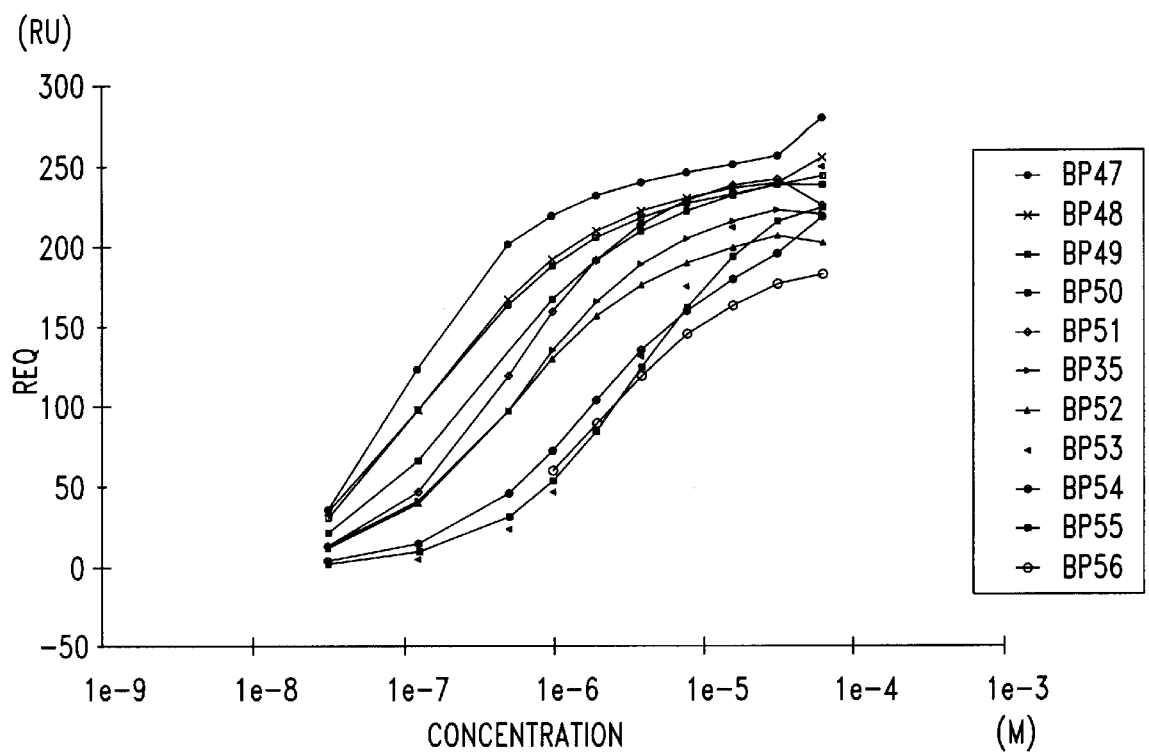
FIG. 3 is a plot of binding curves for a number of oligoprobes (BP35, 47–56) to an immobilized p53 derived wild-type (wt) target DNA sequence (BP44).
Figure 4:
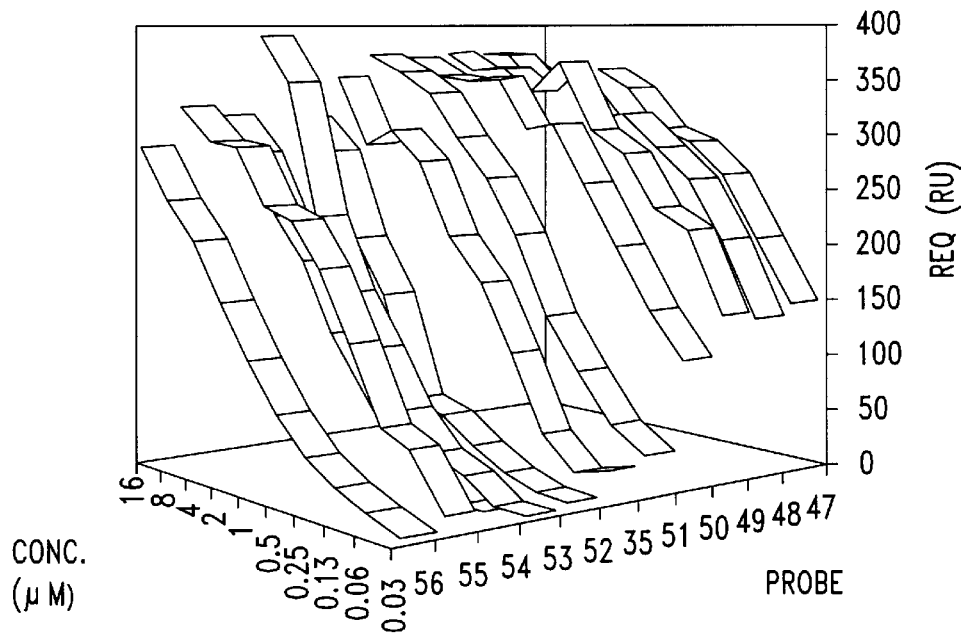
FIG. 4 is another type of plot of the binding curves in FIG. 3.
Figure 5:
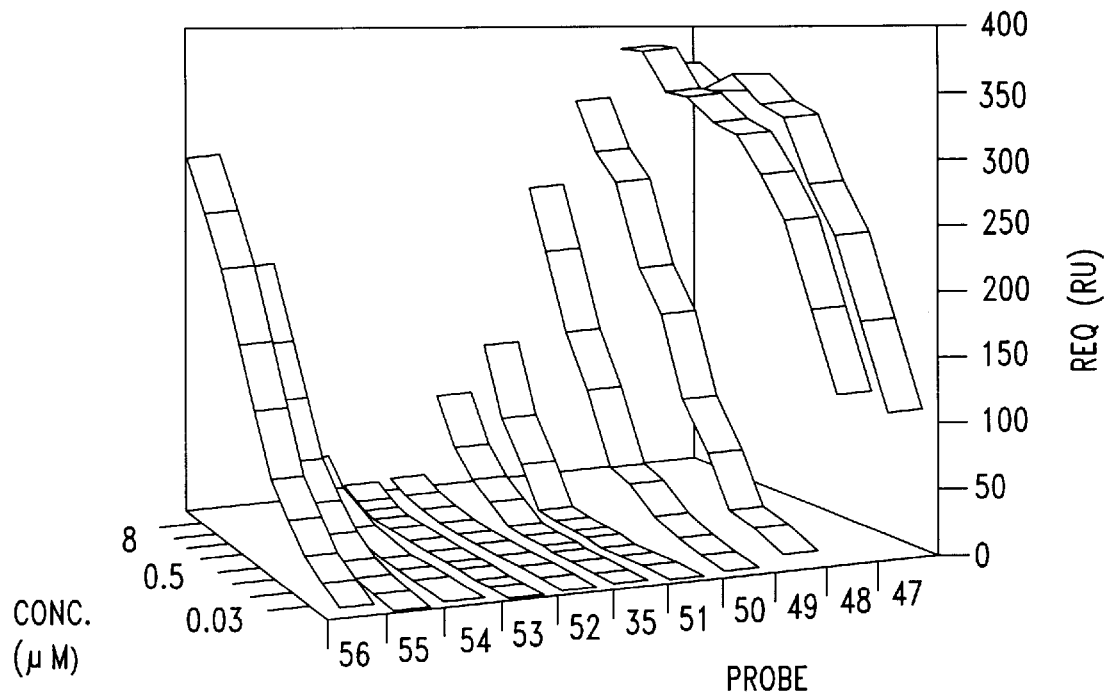
FIG. 5 is a corresponding plot to that in FIG. 4 showing the binding of the same oligomers (BP35, 47–56) to a mutant target DNA sequence (BP45)
Figure 6:
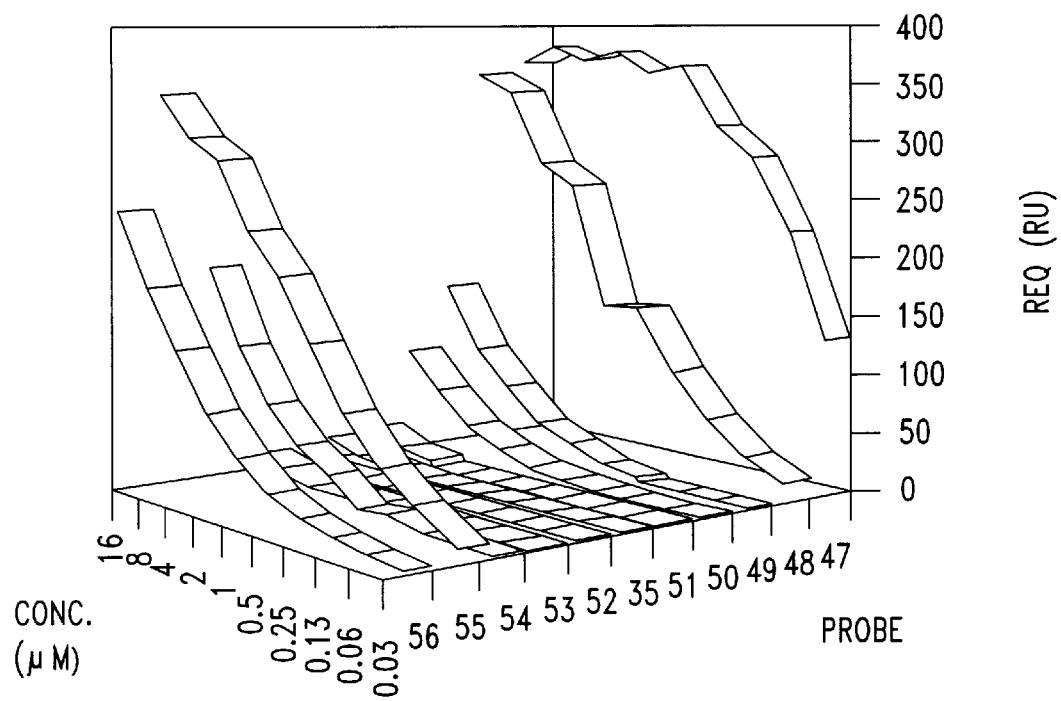
FIG. 6 is a corresponding plot to that in FIG. 5 showing the binding of the same oligomers (BP35, 47–56) to another mutant target DNA sequence (BP46).
Figure 7:
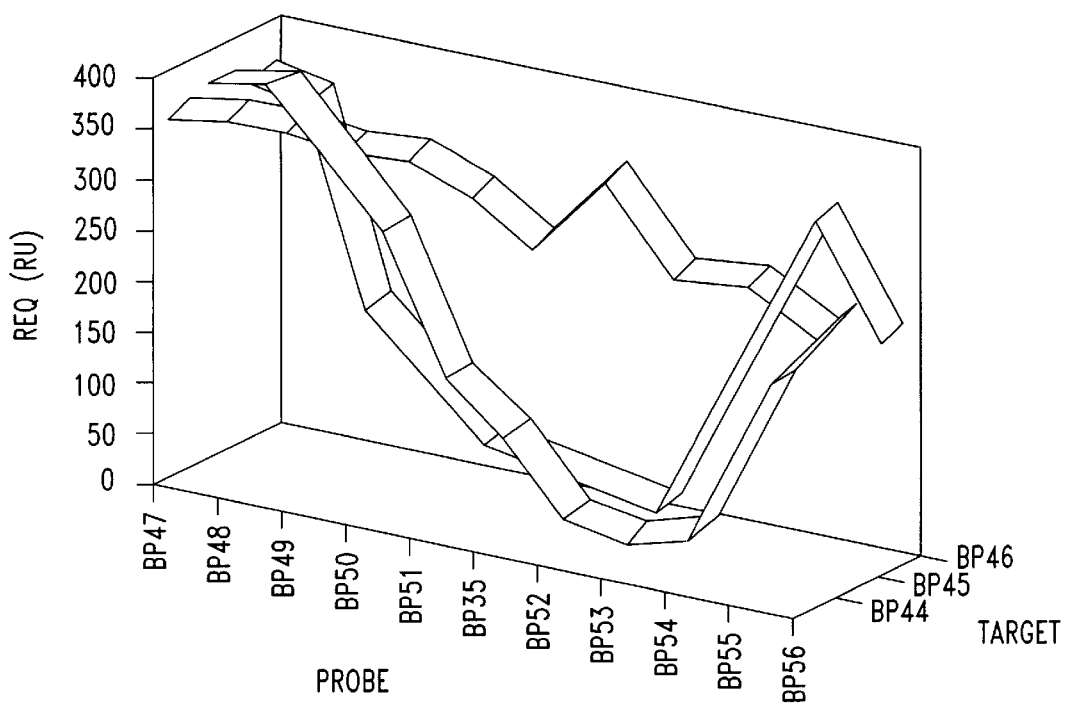
FIG. 7 is a resume of the binding curves in FIGS. 4 to 6.

In the first experiment, the binding of probes BP35 and BP47–56 to the target BP44 was tested. The concentration range was 31 nM–64 μM and the binding curves obtained are presented in FIG. 3. A striking observation is that the range of affinity is quite wide for these 8-mer probes spanning from $2\times10^5$–$6\times10^6$ $M^{-1}$. A fairly good correlation between the affinities obtained and Tm-values calculated as $2\times n(A+T)+4\times n(G+C)$ was found. FIG. 4 shows the binding curves of the probes on the "wt"-target. By comparing this figure to FIG. 5, which shows corresponding binding curves on a mutant target (BP45), where C was changed to T, the effect of single base pair mismatch is clearly demonstrated. The position of the mismatch has a dramatic effect on binding. The same effect is seen in FIG. 6 with target BP46, where T was changed to A. FIG. 7 is a resume of FIGS. 4–6, showing only the $R_{eq}$-responses of the highest concentrations of each probe. The "U-shaped profiles" of the mutant targets differ clearly from the profile of the wt-target, suggesting that it is possible to discriminate perfectly matched probes from end mismatched ones. Comparing the highest response for each probe was found to be discriminative.

Example 2

Hybridization of Different Target DNA Sequences to Immobilized Oligoprobes Under Equilibrium Conditions A new set of modified oligonucleotides based on those described above was designed. Three biotinylated probes

```
5'-B-tttCCTCAGCATCTTATCCGAGttt    BP44 (SEQ ID NO:2)      "wt"

5'-B-tttCCTCAGCATTTTATCCGAGttt    BP45 (SEQ ID NO:3)      "mutC>T"

5'-B-tttCCTCAGCAACTTATCCGAGttt    BP46 (SEQ ID NO:4)      "mutT>A"

GGAGTCGT              BP47 (SEQ ID NO:5)

GAGTCGTA              BP48 (SEQ ID NO:6)

AGTCGTAG              BP49 (SEQ ID NO:7)

GTCGTAGA              BP50 (SEQ ID NO:8)

TCGTAGAA              BP51 (SEQ ID NO:9)

CGTAGAAT              BP35 (SEQ ID NO:10)

GTAGAATA              BP52 (SEQ ID NO:11)

TAGAATAG              BP53 (SEQ ID NO:12)

AGAATAGG              BP54 (SEQ ID NO:13)

GAATAGGC              BP55 (SEQ ID NO:14)

AATAGGCT              BP56 (SEQ ID NO:15)

TCGTAGAT              BP57 (SEQ ID NO:16)

ACGTAGAA              BP58 (SEQ ID NO:17)

GAATAGGG              BP59 (SEQ ID NO:18)

CAATAGGC              BP60 (SEQ ID NO:19)

CGTTGAAT              BP61 (SEQ ID NO:20)

CGTAAAAT              BP62 (SEQ ID NO:21)
``` containing an 8-mer complementary sequence with a spacer tri-T in the 5'-end were constructed. Two 19-mer targets, one "wild-type" and one "mutant" with C changed to T, were also constructed.

```
5'-CCTCAGCATCTTATCCGAG        BP68 (SEQ ID NO:22)  "wt"

5'---------T-----------        BP69 (SEQ ID NO:23)  "mutC>T"

GTAGAATAttt-B-5'     BP63 (SEQ ID NO:24)

AGTCGTAGttt-B-5'        BP64 (SEQ ID NO:25)

GAATAGGCttt-B-5'  BP66 (SEQ ID NO:26).
```

BP68 and 69 correspond to BP44 and 45, except that they are not biotinylated and the extra tri-T ("ttt") of either end has been deleted. BP63, 64 and 66 correspond to BP52, 49 and 55, respectively.

Figure 8:
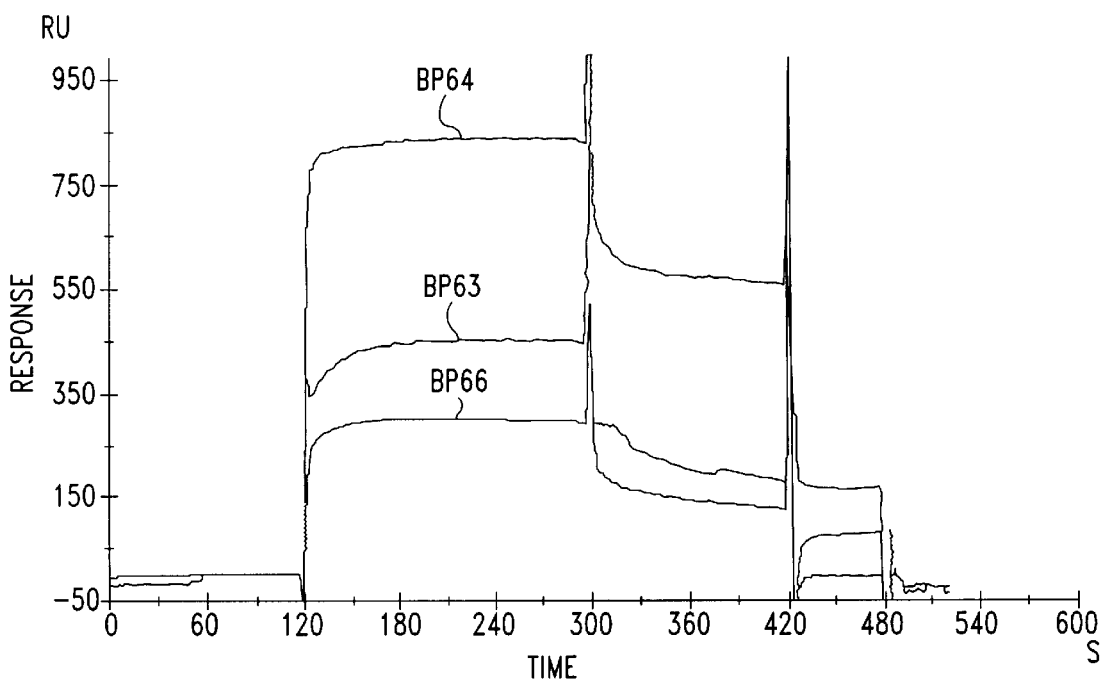
FIG. 8 is an overlay plot of sensorgrams for the binding of a wt target DNA (BP68) to a set of immobilized oligoprobes (BP63, 64 and 66).
Figure 9:
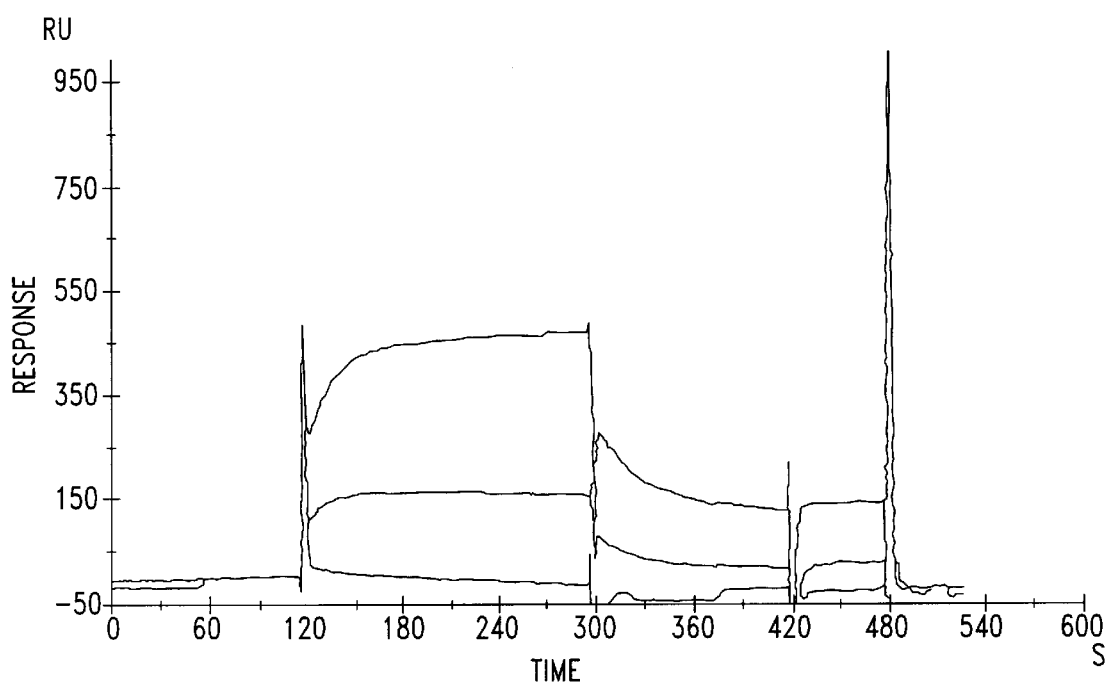
FIG. 9 is an overlay plot of sensorgrams for the binding of a mutant target DNA (BP69) to a set of immobilized oligoprobes (BP63, 64 and 66).

BP63, 64 and 66 were captured in Fc1–3 (554, 782 and 651 RU, respectively) and BP68 and 69 were passed over the flow cells in a serial mode. The concentrations used were 63 nM–64 $\mu$M. The results are shown in the sensorgrams in FIG. 8 (BP68) and FIG. 9 (BP69), where the binding of the two targets to the three probes are compared (blank surface sensorgram is subtracted). As seen in the Figures, the wt target binds to all probes, but with different affinities. BP64 binds best, then BP63 and finally BP66 with the lowest affinity. The mutant target shows reduced binding to all three probes, with no binding at all to BP63. This is the probe with the central mismatch. Thus, the 5'- and 3'-end mismatched probes still bind the target, but with about half the $R_{eq}$-response of the wt target. However, the binding deviates sligthly from that obtained in the straight mode; the on-rate is slightly lower and the binding looks more stable. At the lower concentrations, no steady-state is attained, but a slow binding is observed. The $R_{eq}$-responses were used to estimate the affinities via BIAeval™. In Table 1 below, the values obtained are demonstrated.

TABLE 1

| Target | Probe | Mismatch | $K_A$ (M$^{-1}$) |
| --- | --- | --- | --- |
| BP68 (wt) | BP63 | no | 1.5 × 10$^5$ |
| BP68 (wt) | BP64 | no | 3.2 × 10$^5$ |
| BP68 (wt) | BP66 | no | 3.1 × 10$^5$ |
| BP69 (mutant) | BP63 | internal | — |
| BP69 (mutant) | BP64 | 5'-end | 0.5 × 10$^5$ |
| BP69 (mutant) | BP66 | 3'-end | 0.3 × 10$^5$ |

Thus, also the reversed mode shows a clear discrepancy between end mismatch and internal mismatch. Also in this experiment, 5'-end mismatch has less effect than 3'- dito with respect to affinity.

As demonstrated above, an analysis of oligonucleotide hybridisation can be performed by measuring annealing under equilibrium conditions. The measurements are performed near or above the Tm-values of the 8-mer probes, which allows a very sensitive analysis. This is a major advantage compared to many other methods, where stringency conditions must be very carefully selected if precision should not be sacrificed. The analysis is fast, less than 3 minutes contact time, about 5 min/cycle, and regeneration is not needed. Fully matched 8-mer probes bind with $\mu$M-order affinity (25° C., 0.5 M salt).

Example 3

A series of oligoprobes BP47–BP51, BP35 and BP52–56 were introduced into BIAcore® 2000 with immobilized target wild-type (wt) BP44 and mutant variant BP45 on different surfaces passed in series by the liquid flow. The experiment was run at 30° C. at 32 $\mu$M concentration of the different oligoprobes diluted in buffer. The flow rate was 15 $\mu$l/min and the injected sample volume was 30 $\mu$l. The results are shown in FIG. 10.

As seen in the Figure, the dilution gave rise to a dilution effect during the sample introduction and a rapid decrease in response signal during the sample pulse. The diamond (♦) labelled curve (thick line) shows the interaction with target BP45 mutant and the thin line shows the interaction with wt BP44. During the washing phase between the introduction of the respective oligoprobes BP47–51, a dissociation signal can be seen in the wt response curve, whereas the dissociation for the other oligoprobes was rapid at the temperature used and cannot be resolved from the change in buffer composition. As is clearly demonstrated in the Figure, the response levels for wt and mutant were different over the experiment where oligoprobes passes over the mutant position.

Figure 10:
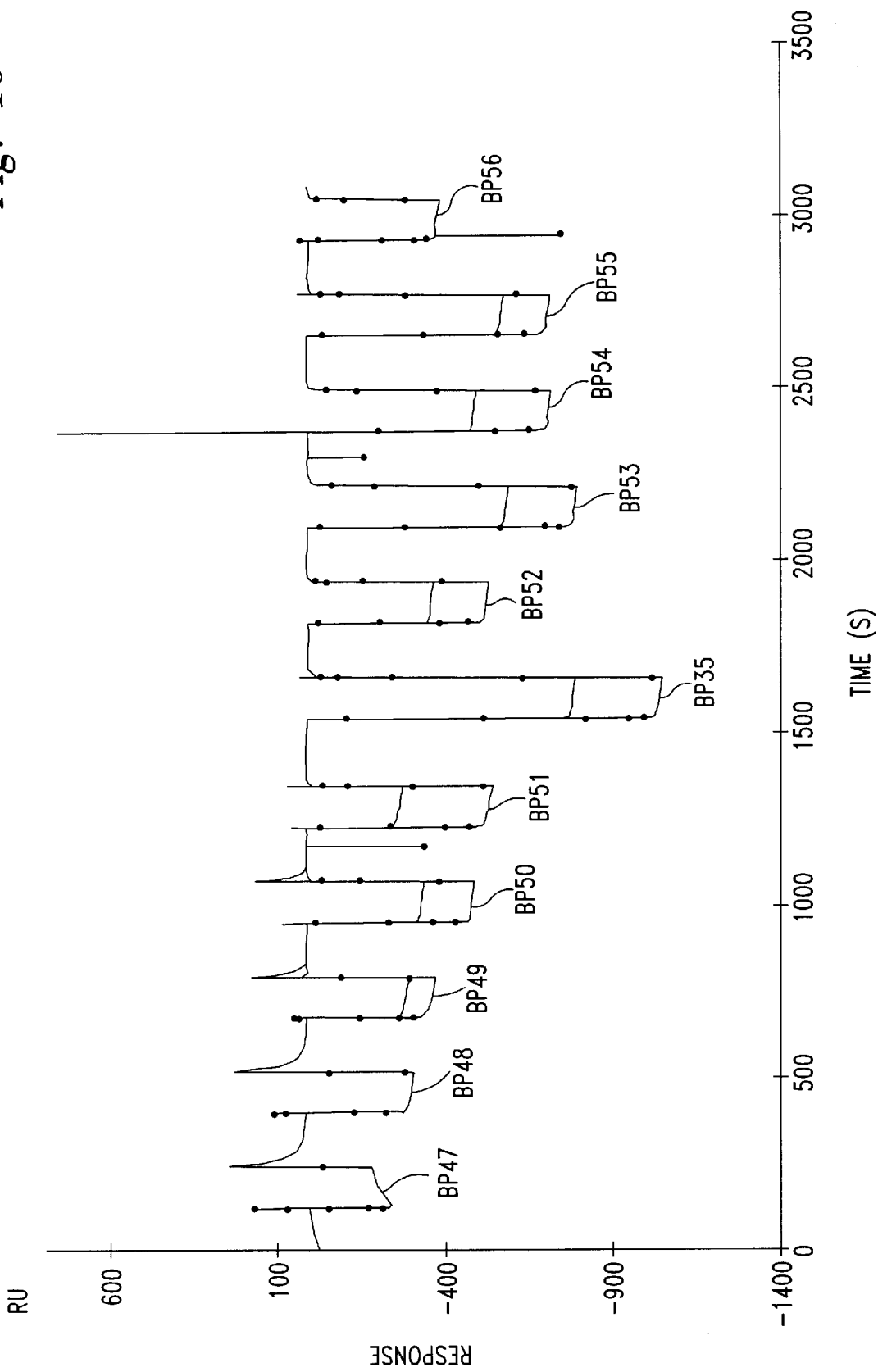
FIG. 10 is an overlay sensorgram showing the sequential hybridization of a series of oligoprobes (BP47–51, BP35, BP52–56) to a target wild-type (wt) DNA (BP44) and mutant DNA (BP45) in series.
Figure 11:
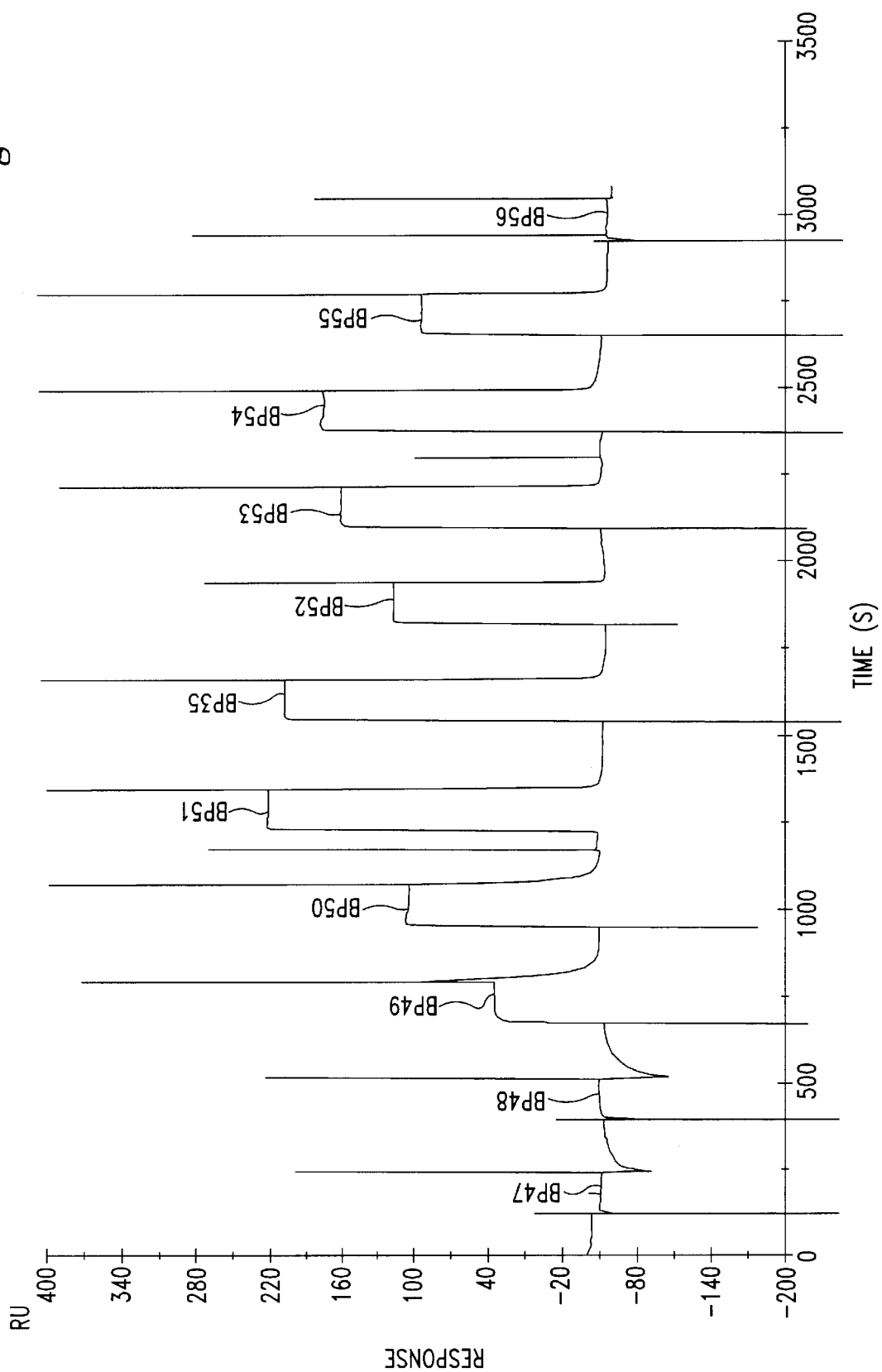
FIG. 11 is a diagram showing a subtraction of the two sensorgrams for the wt and mutant target DNA in FIG. 10 from each other.

FIG. 11 shows a subtraction of the two sensorgrams in FIG. 10 from each other, demonstrating that the difference in response under the annealing conditions gave rise to an increase in signal at the position of a mutation in the mini-sequencing type procedure performed. The diagram shows that the mutation starts with BP49 and ends with BP55 where the difference in signal is well separated from the baseline. (The spikes in the diagram are due to the short time differences for the sample to pass over the two different surfaces with wt and mutant target DNA, respectively.)

Example 4

Figure 12:
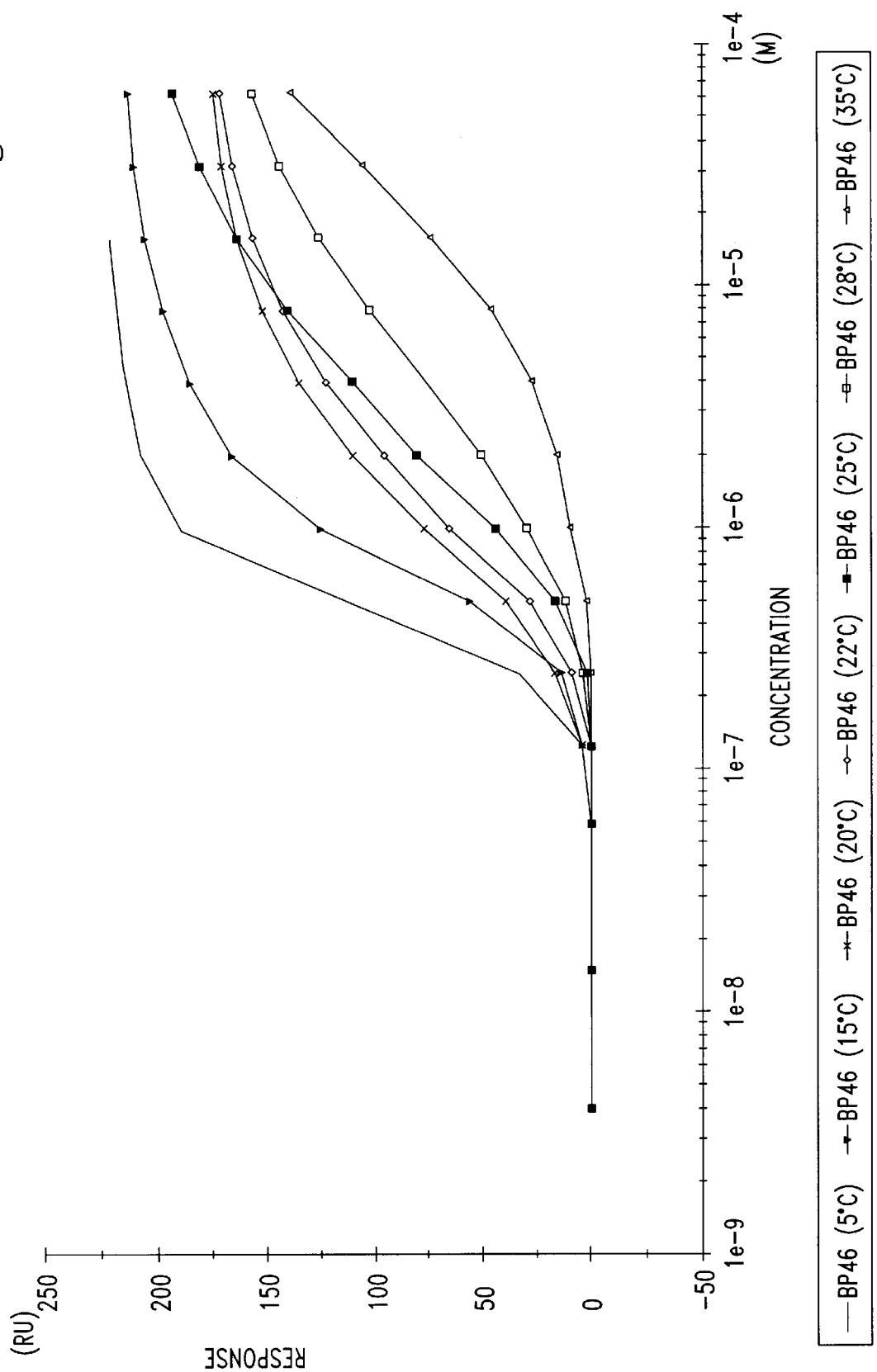
FIG. 12 is a plot of binding curves (equilibrium response vs concentration) for the hybridization of an oligoprobe (BP61) to an immobilized target DNA (BP46) at different temperatures.

The response at equilibrium for the interaction of oligoprobe BP 61 in full match with immobilized target BP 46 was studied at different concentrations and different temperatures ranging from 5 to 35° C. The experiment was run in buffer 2×SSC, a citrate buffer with 0.3 M NaCl, pH about 7. The flow rate was 15 $\mu$l/min and the injected sample volume was 45 $\mu$l. The results are shown in FIG. 12.

The affinity was calculated in the same way as in Example 1, and Table 2 below gives the values for both the obtained equilibrium association affinity constant ($K_A$) and the corresponding dissociation rate constant ($k_{diss}$) for the studied temperatures.

TABLE 2

| Temp. (° C.) | $K_A$ | $k_{diss}$ |
| --- | --- | --- |
| 5 | 1.51 × 10$^6$ | 2.49 × 10$^{-3}$ |
| 15 | 9.31 × 10$^5$ | 0.02 |
| 20 | 6.74 × 10$^5$ | 0.11 |
| 22 | 5.13 × 10$^5$ | 0.14 |
| 25 | 2.83 × 10$^5$ | >0.2 |
| 28 | 2.01 × 10$^5$ | >0.2 |
| 35 | 3.74 × 10$^4$ | >0.2 |

We claim:

1. A method of analyzing nucleic acid sequences, which method comprises measuring by surface sensitive detection technique the binding interaction between a first nucleic acid sequence and a second nucleic acid sequence, one of the first and second nucleic acid sequences being immobilized to a solid phase surface, to determine the affinity or an affinity related parameter for the binding reaction as indicative of the extent of complementarity between the first and second nucleic acid sequences, wherein the measurement of the binding interaction is performed at annealing conditions adjusted such that the dissociation rate constant for the binding interaction corresponding to full complementarity between the first and second nucleic acid sequences is greater than $10^{-3}$ per second, thereby permitting equilibrium for the interaction to be rapidly attained.

2. The method according to claim 1, wherein said measurement is performed at equilibrium.

3. The method according to claim 1, wherein the dissociation rate constant is greater than $10^{-2}$ per second.

4. The method according to claim 1, wherein the first nucleic acid sequence is at least one oligonucleotide probe and the second nucleic acid sequence is at least one target nucleic acid sequence to be sequence analyzed.

5. The method according to claim 1, wherein the first nucleic acid and second nucleic acid sequences independently are single- or double-stranded DNA or RNA or single-stranded DNA or RNA complexed with a different molecule wherein the different molecule is a molecule other than the single-stranded DNA or RNA.

6. The method according to claim 1, wherein said adjustment of the annealing conditions comprises adjusting the temperature and/or the reaction medium.

7. The method according to claim 4, wherein said oligonucleotide probe or probes are bound to the solid phase surface.

8. The method according to claim 7, wherein the method comprises the additional step of analyzing the dissociation constant for the binding reaction to determine therefrom the possible presence of repeated sequences in the target nucleic acid sequence.

9. The method according to claim 4, wherein the target nucleic acid sequence is bound to the solid phase surface.

10. The method according to claim 9, wherein the method comprises scanning the target nucleic acid sequence for a mutation or mutations with a first set of oligonucleotide probes to detect a mutated part or parts of the target sequence, and then testing a detected mutated part or parts of the target sequence with a second set of oligonucleotides to determine the position of the mutation or mutations and optionally the corresponding base change.

11. The method according to claim 1, wherein said first or second nucleic acid sequences are immobilized in an array at defined positions on the solid phase surface.

12. The method according to claim 1, wherein the method comprises the additional step of determining the concentration of the first or second nucleic acid sequence at diffusion rate limited conditions.

13. The method according to claim 1, wherein said surface sensitive detection technique is based on evanescent wave sensing.

14. The method according to claim 1, wherein the measurement is performed in a flow cell.

\* \* \* \* \*